United States Patent [19]

Rosenthal

[11] Patent Number: 4,798,955

[45] Date of Patent: Jan. 17, 1989

[54] MEASUREMENT LOCATOR AND LIGHT SHIELD FOR USE IN INTERACTANCE TESTING OF BODY COMPOSITION AND METHOD FOR USE THEREOF

[75] Inventor: Robert D. Rosenthal, Gaithersburg, Md.

[73] Assignee: Futrex, Inc., Gaithersburg, Md.

[21] Appl. No.: 100,226

[22] Filed: Sep. 23, 1987

[51] Int. Cl.⁴ ............................................. G01N 21/01
[52] U.S. Cl. ................................. 250/341; 128/633; 250/339
[58] Field of Search ................. 250/339, 341; 128/633, 128/634, 664, 68.1, 132 D

[56] References Cited

U.S. PATENT DOCUMENTS

| | | | |
|---|---|---|---|
| 3,812,842 | 5/1974 | Rodriguez | 378/163 |
| 4,380,240 | 4/1983 | Jöbsis et al. | 128/633 |
| 4,442,844 | 4/1984 | Navach | 128/663 |
| 4,466,076 | 8/1984 | Rosenthal | 364/571 |
| 4,510,933 | 4/1985 | Jöbsis et al. | 128/633 |
| 4,608,990 | 9/1986 | Elings | 128/633 |
| 4,633,087 | 12/1986 | Rosenthal et al. | 250/341 |

OTHER PUBLICATIONS

Joan M. Conway, PhD., Karl H. Norris, BS, and C. E. Bodwell, PhD; "A New Approach for the Estimation of Body Composition: Infrared Interactance"; *The American Journal of Clinical Nutrition*, 40; (Dec. 1984) pp. 1123-1130.

*Primary Examiner*—Janice A. Howell
*Assistant Examiner*—Constantine Hannaher
*Attorney, Agent, or Firm*—Bernard, Rothwell & Brown

[57] ABSTRACT

A light barrier and probe location device are disclosed for use with a near infrared interactance probe for measuring body composition on the upper arm of an individual while allowing the individual to conduct his/her own test at the same position on the arm each time and excluding ambient light. The device includes a piece of opaque material having an opening for the light probe, a probe location member removably attached to the material to position the light probe location opening and fastening means for attaching the opaque material around the arm of an individual after the probe location member locates the appropriate opening position to allow the individual to conduct his/her own test on him/herself.

7 Claims, 2 Drawing Sheets

MEASUREMENT LOCATOR AND LIGHT SHIELD FOR USE IN INTERACTANCE TESTING OF BODY COMPOSITION AND METHOD FOR USE THEREOF

BACKGROUND OF THE INVENTION

1. Field of the Invention

This invention relates to improvements in connection with measurements for estimating body composition, particularly of the type using near-infrared interactance. More particularly, this invention relates to a measurement locator and light shield for use with an interactance probe while conducting such measurements and a method for use thereof.

2. Description of the Prior Art and Problem Involved

The United States Department of Agriculture (USDA) has demonstrated that light absorption can measure the chemical constituents within organic products. One application of this technology was described in the technical paper "A New Approach for Estimation of Body Composition: Infrared Interactance" published in the American Journal of Clinical Nutrition, 40, Dec., 1984, pp. 1123-1130. In this paper the USDA described and demonstrated that measurement of body fat can be made by performing optical measurements on the biceps (i.e., half way between the elbow and the shoulder of the prominent arm—the prominent arm is the arm that is used for writing).

An adaptation of this technique was patented by Robert D. Rosenthal, et al. and assigned to Trebor Industries, Inc. of Gaithersburg, Maryland in U.S. Pat. No. 4,633,087 granted Dec. 30, 1986. In this Rosenthal, et al. patent a low-cost "light wand" is disclosed to make measurements similar to those mentioned in the USDA paper. The Rosenthal, et al. technique was further improved in patent application Ser. No. 058,550, filed June 5, 1987, of Rosenthal, et al. which provides and obtains an increase in precision of the measurement by adding narrow bandpass optical filters.

This type of quantitative in vivo measurement of body composition is expected to have many applications in human diagnostic functions in the next several years. However, the present state of the art leaves unsolved three fundamental problems which are required in addition to having a proper "light wand and measurement system." These additional unsolved problems include:

1. The fact that external light can "wash out" the measurement, thus the need to exclude all external light so that the measurement is not "washed out".
2. The necessity for taking the measurement at precisely the same point on the body of the individual being measured each time the measurement is made so that a proper comparative measurement can be obtained.
3. The need for a second person to perform the required measurement and the test on the individual, i.e., the need for an outside operator detracts from the versatility of the prior art.

All three of the above-mentioned problems are solved with the simple device and method of this invention.

The previous approach to using such instruments was to use another person (i.e., an operator) to measure the length of the arm between the shoulder and the inside of the elbow of the person undergoing the test (test person). The operator would then mark the location on the arm of the test person and then place the flexible light probe at the properly located marked point. A small flexible optically opaque light shield affixed around the probe would attempt to protect the measurement from ambient light. Although this previous approach worked fairly well, it had the following limitations:

1. It required an outside person (the operator) to measure the length of the arm each time the tested person is to be tested. This slows down the measurement process and leads to possible errors in the location of the measurement.
2. Depending on how well the light seal gasket is used, external light may or may not interfere. An individual's arm, by its very nature, is quite transparent to light in the near infrared spectrum, thus if the measurements are taken in sunlight or in other broad spectrum light, the arm must be totally enclosed which causes a further problem for the outside operator.
3. The use of a second person or outside operator is required in order to accomplish the test, thus the test cannot be self-administered.

SUMMARY OF THE INVENTION

This invention provides a simple solution to all of the above problems. The solution is the use of a piece of flexible, drapable, opaque material having an opening for the probe therein with the material being sufficiently large to overwrap the arm of the individual. Separated fastening means on one side of the piece of opaque material are provided for allowing the material to be closed around the arm of the individual. A removably attached measurement locator or probe locating member is removably attached to the piece of opaque material in a position to determine the precise location of the probe opening when the member gauges an individual's arm so that the light shield and hence the probe can be repeatedly positioned at the precise position on the arm. Fastening means are utilized for both fastening the piece of opaque material around the arm and for fastening the locator to the opaque material to allow easy opening and removal.

BRIEF DESCRIPTION OF THE PREFERRED EMBODIMENT

Figure 1:
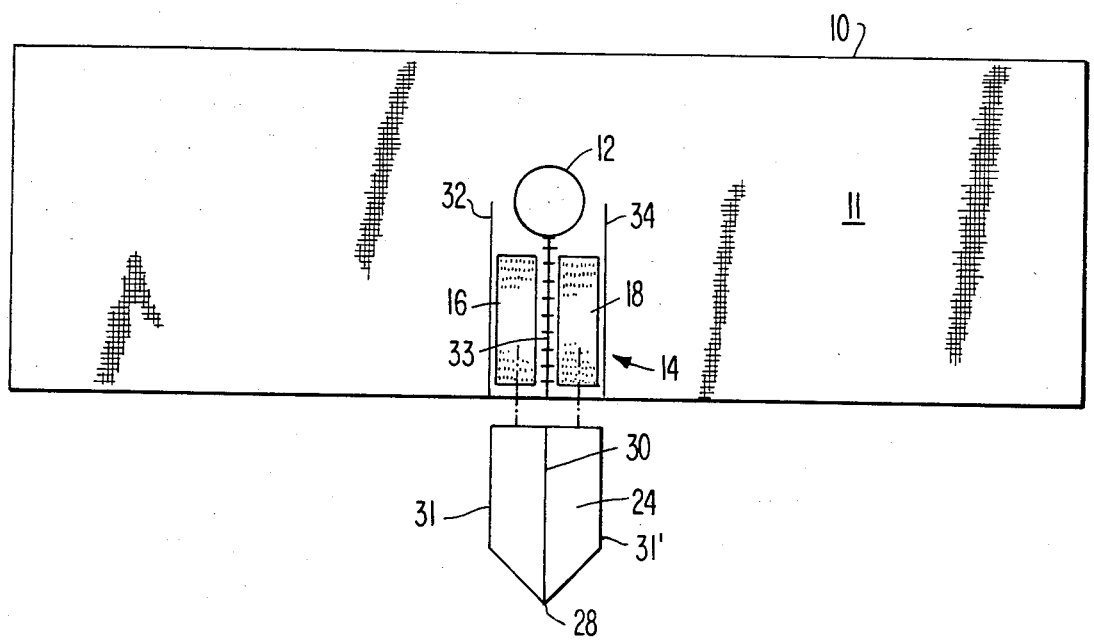
FIG. 1 is a top plan view of the measurement locator and light shield prior to their being assembled together.
Figure 4:
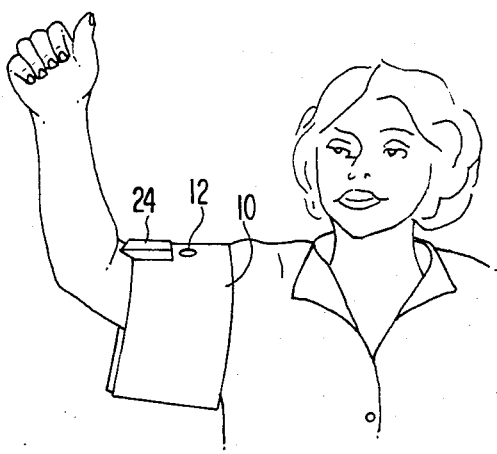
FIGS. 4, 5, and 6 show steps in the use of the device of this invention and carrying out the method of this invention.

A piece of drapable, flexible, opaque material 10 is formed of a sufficient size to drape over a person's arm, see FIG. 4. The material can, for example, be formed of black plastic and can be of rectangular shape as shown in FIG. 1. The material has an opening 12 formed therein of a diameter sufficient for a "light wand" as described in the above-mentioned patent and application.

On one face 11 of the material there is a fastening means 14 in the form of parallel strips 16 and 18 of hook and loop fasteners (Velcro®) or any other type of suitable fastening means.

Figure 2:
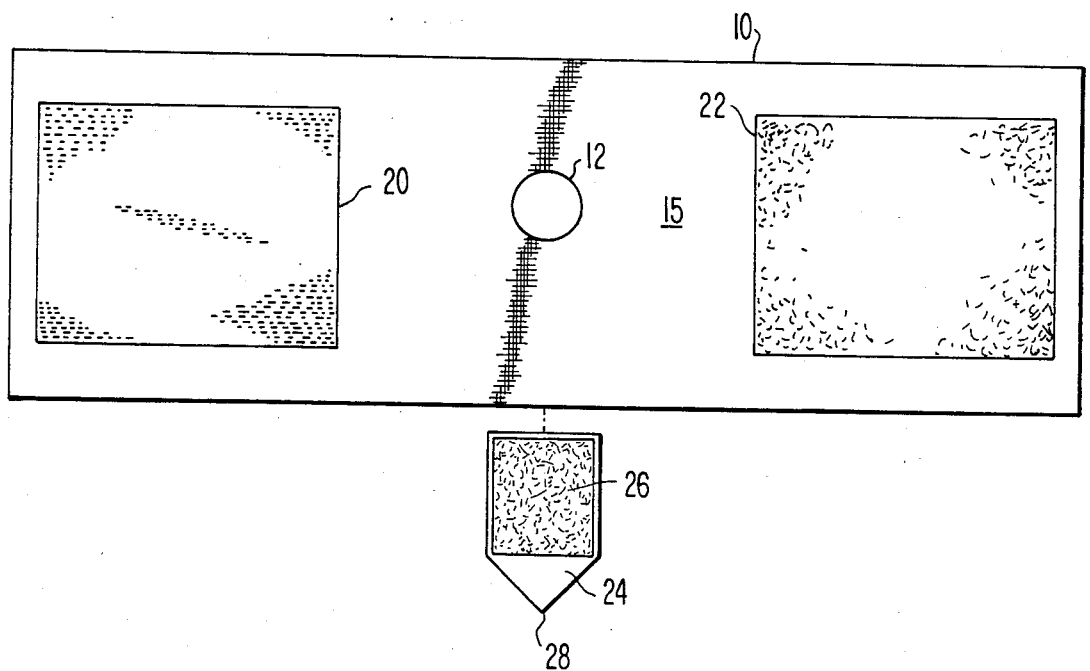
FIG. 2 is a bottom plan view of the measurement locator and light shield prior to their being assembled together.
Figure 3:
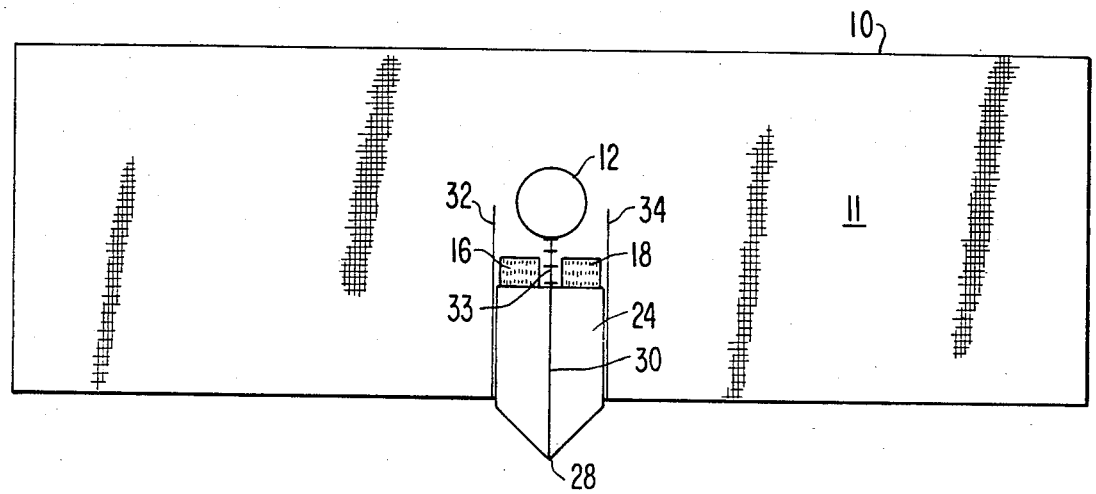
FIG. 3 is a top plan view of the measurement locator and light shield after assembly.
Figure 5:
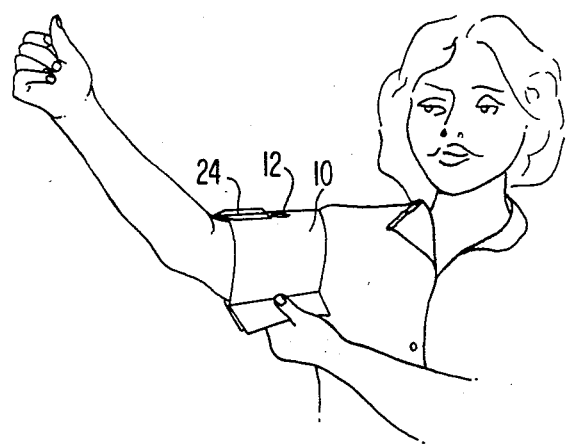

As shown in FIG. 2 on the other face 15 of the piece of flexible opaque material 10 there are similarly spaced fastening means of hook and loop fasteners 20, 22 or any other suitable fasteners which can allow the areas of the face 15 to be fastened together around the user's arm (See FIG. 5).

A separate measurement locator 24 has fastening means 26 on its back side for mating with the fastening means 16, 18 on the face 11 of material 10 at a precise position. The measurement locator may have a suitable point or other surface 28 at one end with flat side edges 31, 31' so that it may be positioned on the material 10 in the desired location while not covering the hole 12. The particular position depends on the user and will be described hereinafter.

The use of the measurement locator and light shield for carrying out the method of this invention will now be described. The measurement locator has a line 30 down its center and this line, plus the two side edges 31, 31' are utilized for location by aligning them with three lines 32, 33, 34 on the face 11 of the opaque material 10; line 33 also bears a scale for repositioning purposes. These lines show proper orientation of the measurement locator to the opaque material and proper orientation occurs when all three lines on the two pieces of material line up with each other.

In operation of the device, the length of the arm is measured and proper location for the optical probe is determined. The proper location is half way between the shoulder and the inside of the elbow. The measurement locator is then placed on the opaque light shield with the three lines lined up so that the distance from the tip 28 of the measurement locator 24 to the center of the hole 12 is the proper point as determined by the initial measurement. This is done by allowing the tip 28 of the measuring locator 24 to be at the center of the elbow (the "elbow line") and aiming at the thumb while the biceps portion of the arm is raised to a horizontal position and the arm is bent at the elbow in a 90° direction with the forearm pointing upward as shown in FIG. 4.

Once the proper position of the probe hole 12 is located and the measurement locator is attached to the opaque material the size (as indicated by the size indicator scale on line 33) is then recorded. The purpose of recording the number is to allow multiple users of the same unit. If someone changes the size, the current user would not have to again use the ruler to measure and determine the proper size. The current user would simply reset the size, setting it to the prior known size.

The next step in the normal use in the device would be to drape it over the arm aligning the "elbow line" of the measurement locator at the elbow pointing thumbs up. The opposite hand of the individual of whom the measurement is made would clutch the bottom of the material so that the hook and loop or other type fastener material closes the material around the arm. This closure prevents outside light leaks as well as insuring that the properly located measurement hole 12 is maintained at the same position on the tested person's arm. This is shown in FIG. 5.

Figure 6:
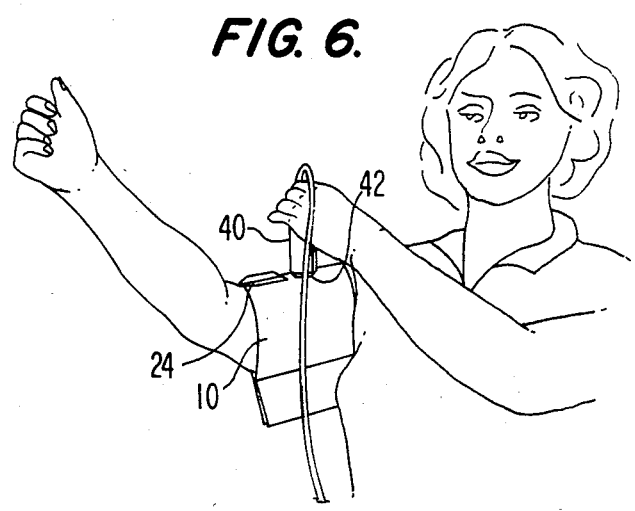

The last step, as shown in FIG. 6, is placing the light probe 40 against the tested person's arm through the probe hole 12. A small rubber gasket 42 may be placed around the probe to make sure that no light leaks around the hole when the probe is being pressed. The device can then be read off digitally on the instrument as described in the prior patent and application (but not shown here).

It is noted that the above device and method eliminate three of the fundamental problems of self-testing with the type of instrument involved. Using the opaque material blocks out all unwanted light no matter what direction the light striking the arm is coming from. In addition, having the probe hole precisely located insures that future measurements are always made at the same location. Moreover, it allows the individual to use the non-prominent arm to seal the drape and perform the probe test without the need for an outside operator.

I claim:

1. A light barrier and probe location device for use with a near infrared radiation interactance probe for measuring body composition on the upper arm of an individual, the device comprising:
    (a) a piece of drapable, flexible opaque material having an opening therein for receipt of the probe at a predetermined position, the material being sufficiently large to overwrap the arm of an individual to be tested,
    (b) adjustable fastening means on the piece of opaque material for removably attaching the piece of opaque material around the upper arm of an individual and allowing it to be held in place to exclude light to a probe inserted into the opening during the test and to be separated for removal from the arm after the test, and
    (c) a probe location member attached to the piece of opaque material in a position to determine the precise location of the probe opening when the opaque drape engages the individual's upturned arm, the probe location member locating on the inside of the elbow of the individual.

2. A device as defined in claim 1 wherein the probe location member is removably attached to the piece of opaque material.

3. A device as defined in claim 2 wherein the removable attachment of the probe location member to the flexible opaque material is by hook and loop fastener means.

4. A device as defined in claim 1 wherein the fastening means for fastening the flexible opaque material around the arm of an individual are separated fastening means.

5. A device as defined in claim 4 wherein the separated fastening means are hook and loop fastener means.

6. A method of quantitative in vivo measurement of the type used for estimating body composition of an individual, the method using a near infrared interactance probe positioned on the biceps of the individual to be measured (tested person), the improved method allowing self-measurement at precisely the same position the biceps and excluding external light, the improved method comprising:
    (a) measuring from the inside of the elbow on the arm of the tested person to determine the probe position,
    (b) setting such measurement on a flexible light shield drape attachment,
    (c) positioning the flexible opaque light shield drape having an access opening for the probe therein on the upper arm of the tested person so that such opening is at a predetermined point within the light shield drape and at a measured distance from the elbow and biceps of the tested person, (d) enclosing the biceps portion of the tested person's arm with the opaque light shield drape, the drape holding itself in position, and (e) inserting the near infrared interactance probe in the opening in the flexible opaque light shield drape while it is in position by the tested person while the drape is closed in order to measure the body composition of the individual.

7. A method as in claim 6 wherein the positioning of the flexible light shield drape is accomplished by attaching a removable location member at a precise position relative to the drape and contacting the location member with the inside of the elbow of an upturned arm of the tested person.

* * * * *

UNITED STATES PATENT AND TRADEMARK OFFICE
CERTIFICATE OF CORRECTION

PATENT NO. : 4,798,955

DATED : JANUARY 17, 1989

INVENTOR(S) : ROBERT D. ROSENTHAL

It is certified that error appears in the above-identified patent and that said Letters Patent is hereby corrected as shown below:

Column 4, line 55, delete "position" and substitute therefor -- point on --.

Signed and Sealed this

Thirteenth Day of February, 1990

Attest:

JEFFREY M. SAMUELS

*Attesting Officer*   *Acting Commissioner of Patents and Trademarks*